(12) United States Patent  
Murray

(10) Patent No.: US 6,464,728 B1  
(45) Date of Patent: Oct. 15, 2002

(54) MODULAR NECK FOR FEMUR REPLACEMENT SURGERY

(76) Inventor: Ian P. Murray, 14351 Hampshire Knob Dr., Phoenix, MD (US) 21131

( * ) Notice: Subject to any disclaimer, the term of this patent is extended or adjusted under 35 U.S.C. 154(b) by 0 days.

(21) Appl. No.: 09/505,876

(22) Filed: Feb. 17, 2000

Related U.S. Application Data

(63) Continuation-in-part of application No. 09/059,698, filed on Apr. 14, 1998, now abandoned.

(51) Int. Cl.⁷ .................................................. A61F 2/36
(52) U.S. Cl. ................................. 623/22.42; 623/22.46; 623/23.23; 623/23.48
(58) Field of Search ........................... 623/19.11–19.14, 623/22.11–23.38, FOR 19, FOR 22, FOR 23

(56) References Cited

U.S. PATENT DOCUMENTS

| 4,888,023 A | 12/1989 | Averill et al. |
| 4,892,546 A | 1/1990 | Kotz et al. |
| 4,919,670 A | 4/1990 | Dale et al. |
| 4,995,883 A | 2/1991 | Demane et al. |
| 5,002,578 A | 3/1991 | Luman |
| 5,002,581 A | 3/1991 | Paxson et al. |
| 5,030,234 A | 7/1991 | Pappas et al. |
| 5,057,101 A | 10/1991 | Dorr et al. |
| 5,108,452 A | 4/1992 | Fallin |
| 5,286,260 A | 2/1994 | Bolesky et al. |
| 5,653,764 A | 8/1997 | Murphy |
| 5,653,765 A | 8/1997 | McTighe et al. |

FOREIGN PATENT DOCUMENTS

| EP | 0 201 407 A1 | 11/1986 | |
| EP | 0 187 903 B1 * | 1/1989 | .......... 623/FOR 23 |
| WO | 91/03992 | 4/1991 | |
| WO | WO-94/07438 A * | 4/1994 | .......... 623/FOR 23 |

* cited by examiner

Primary Examiner—David H. Willse  
(74) Attorney, Agent, or Firm—Sam Rosen; Leonard Bloom

(57) ABSTRACT

A prosthesis for femur replacement surgery has a stem which is received in the femur. The stem has a blind bore formed at an angle in the upper portion. A modular neck assembly is received in the blind bore. The neck assembly is formed at a desired angle with respect to the vertical axis of the stem. The neck assembly is keyed to the bore to obtain a desired degree of anteversion and offset by a desired rotation of the neck assembly within the bore. A unitary sleeve may be inserted in a canal in the femur to receive the stem and provide circumferential movement of the prosthesis within the femur canal. A porous coating is formed on the outer surface of the stem and the sleeve.

1 Claim, 6 Drawing Sheets

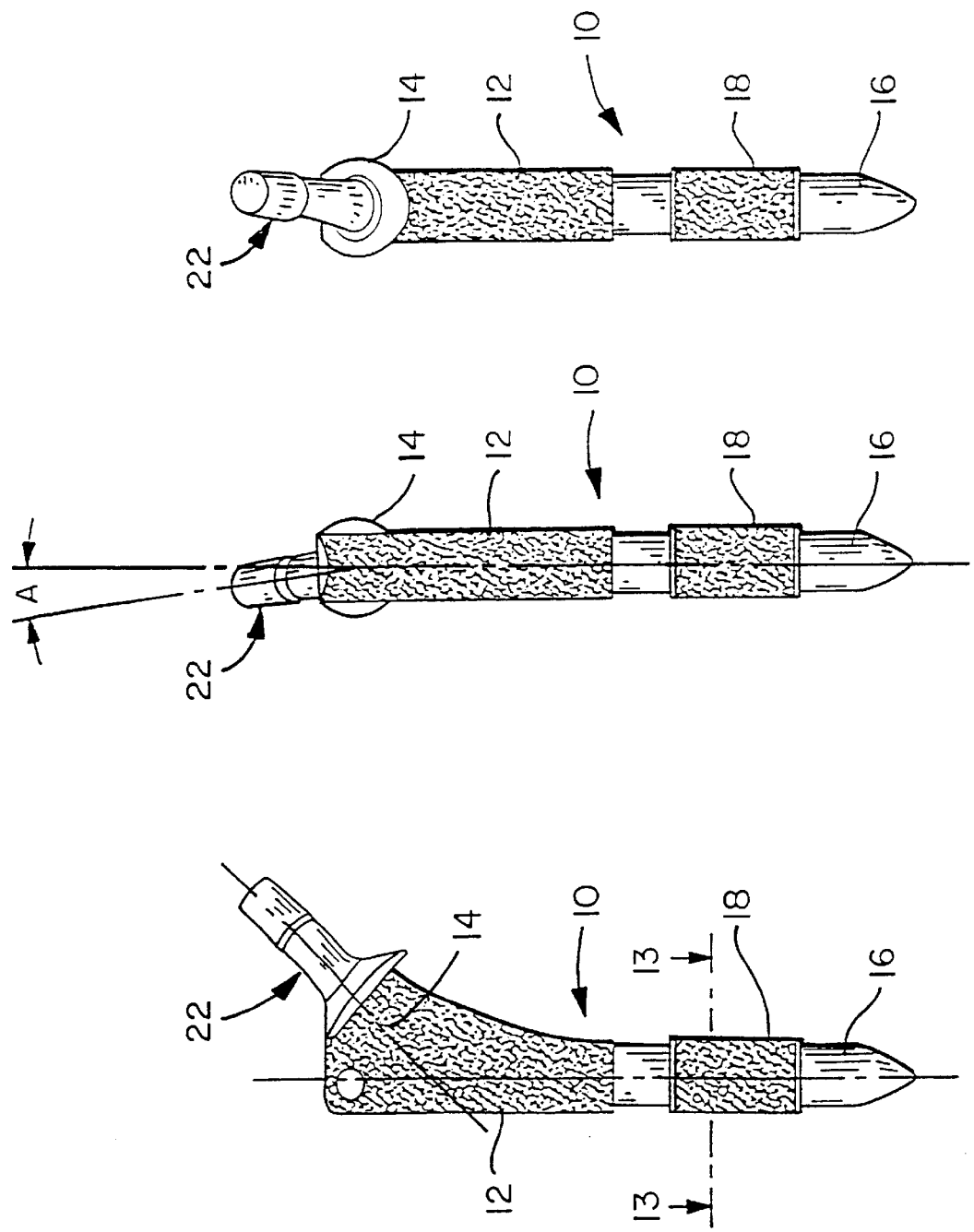

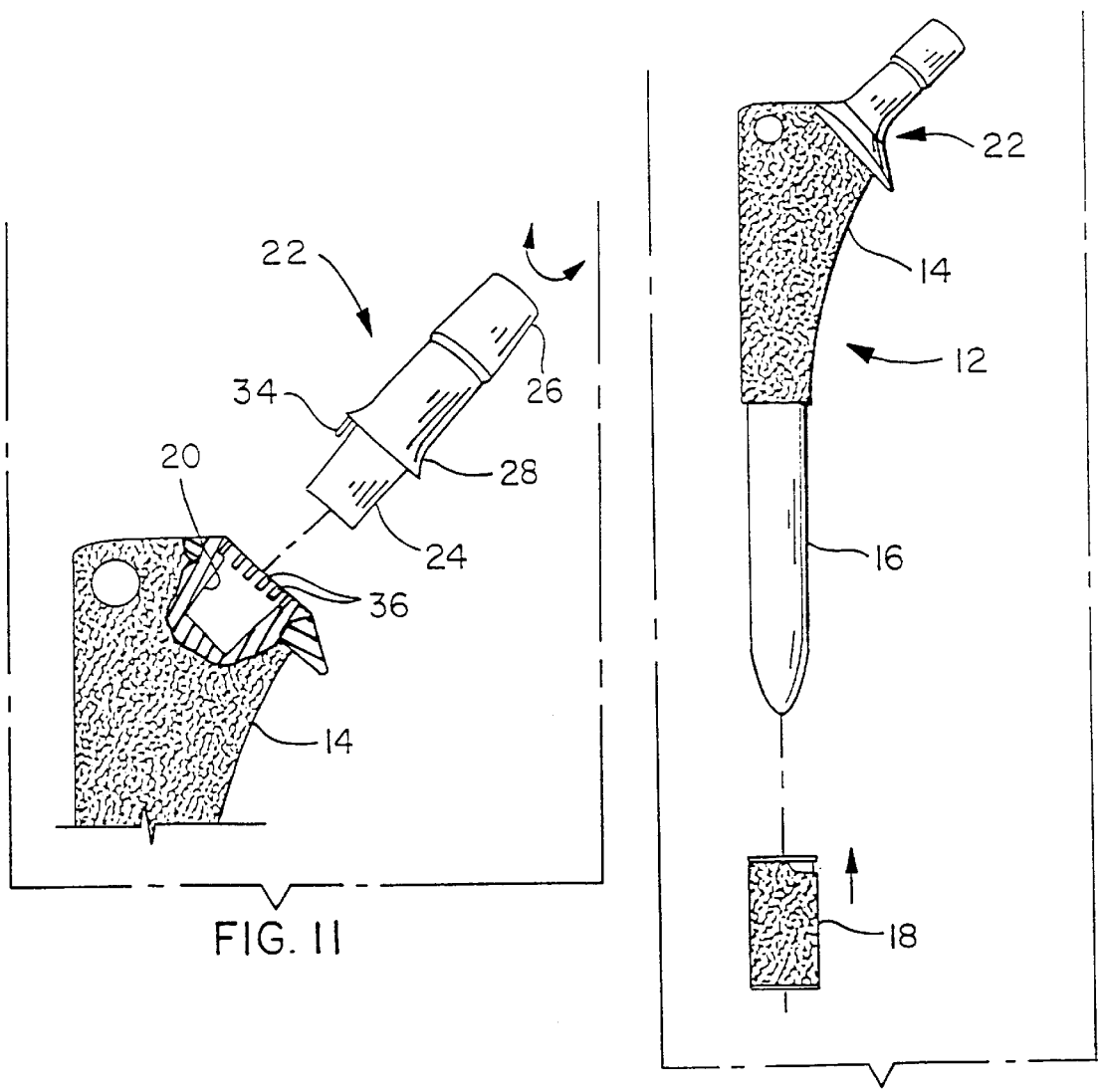
FIG. 11
FIG. 12
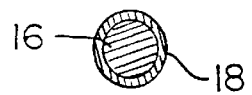
FIG. 13

MODULAR NECK FOR FEMUR REPLACEMENT SURGERY

CROSS REFERENCE TO RELATED APPLICATION

The present invention is a continuation-in-part application of application Ser. No. 09/059,698, filed Apr. 14, 1998, now abandoned, the disclosure of which is incorporated in its entirety by reference herein.

BACKGROUND OF THE INVENTION

The present application relates to a prosthesis for femur replacement surgery and more particularly to a prosthesis which receives a modular neck assembly selected for a desired neck length, neck angle, anteversion and offset.

Surgery to replace the femur in total joint surgery involves the insertion of a stem in a cavity formed in the femur. The end of the stem extending from the cavity has a neck which is formed at an angle and the neck is mated with a socket in the hip. Every patient requires individual fitting due to the unique anatomical requirements of the particular patient. A prosthesis in which the stem and neck are a unitary device requires that the surgeon have a large quantity of prostheses available to provide a correct bio-mechanical function of the prosthesis with the patient. It is very costly to maintain a large inventory of prostheses and, despite the number of prostheses available, quite often the appropriate size and angle are not completely met.

More recently, modular prostheses have been designed to overcome this longstanding problem. The modular designs have each focused on a different aspect of the prosthesis. U.S. Pat. No. 4,919,670 to Dole et al disclose a tapered cylindrical lock mechanism disposed on the proximal end surface of the stem and the head mechanism including a complementary tapered aperture for receiving the cylindrical lock mechanism in a rigid mechanical coupling engagement. In U.S. Pat. No. 4,995,883, Demane et al disclose a modular hip prosthesis which can be custom fitted to a patient before surgery. A plurality of prostheses bodies, pads, heads, collars and extension sleeves are offered in various sizes. An elongated bolt extends through the prosthesis body and is connected to the extension sleeve. Luman, in U.S. Pat. No. 5,002,578 discloses a modular hip stem prosthesis apparatus which includes a hip stem with an integral, enlarged shoulder and a neck section mountable to the hip stem which are releasably interconnected with a bolt. The annular relation between the side arm and the longitudinal axis of the hip stem is selectively predetermined. In U.S. Pat. No. 5,002,581, Paxson et al disclose a modular hip joint prosthesis with adjustable angular variation. This variation is made possible by having the axis of the connection part of the stem and neck being angularly offset from the axis of the body of the stem and neck, respectively. Pappas et al, in U.S. Pat. No. 5,030,234 disclose a modular stem prosthesis which has a stem connected to an extension with a slip fit interconnection. Engagement between the stem and the extension is provided by deflectable end portions of one component of the prosthesis which are engaged in a mating deformation with the other component. Fallin, U.S. Pat. No. 5,108,452, is a continuation-in-part of Demane et al and discloses removable pads attached to the prosthesis body with a wedge to lock the connection between the prosthesis and the hip joint. In U.S. Pat. No. 5,286,260, Bolesky et al disclose a modular hip prosthesis for replacement of a portion of the femur comprising a kit that includes an upper and lower portion. A neck member is also provided to rigidly attach the head member to the body member. McTighe et al in U.S. Pat. No. 5,653,765 disclose a modular hip stem prosthesis having a neck member extending angularly outward from the shoulder piece and configured to receive a spherical hip ball for insertion into the hip socket. A locking screw securely joins the shoulder piece with the stem.

A further complication in the total joint surgery to replace the femur is that clinically, the metal of the prosthesis is not compatible with the bone on a modular scale. The different moduli of the bone and the metal causes a stress path to pass through the more rigid material and the stress between the bone and metal occurs distally shielding the proximal femur from stress. This results in atrophy of the proximal femur and pain to the patient and eventually, possible failure. To alleviate this problem, Averill et al in U.S. Pat. No. 4,888,023, disclosed a prosthesis with a fixation resistant finish on the external peripheral surface of the distal tip. The distal tip is selectively removable and replaceable. In U.S. Pat. No. 4,892,546, Kotz et al disclose an adjustable prosthesis for a joint bone having an elongated inner sleeve and an outer sleeve. The inner sleeve is telescopically slidable within the outer sleeve but is not rotatable. The inner sleeve includes a threaded spindle nut and a threaded spindle which are positioned within the inner sleeve. In U.S. Pat. No. 5,057,101, Dorr et al disclose a femoral prosthesis with a centering sleeve wherein the sleeve is removably attached midway along a stem of the prosthesis. Removable sleeves are disclosed.

Montagne in European Patent No. 0 201 407 A1 discloses a prosthesis with connecting members which are adjustable with an octagonal fitting. A sleeve is not disclosed on the shank of the prosthesis. Frey in European Patent No. 0 187 903 A1 discloses an adjustable hip joint prosthesis with an outer sleeve having an inner polyethylene liner. The outer sleeve has an outer surface with self-tapping threads to be screwed to the femur. In WIPO publication WO 94/07438, Tronzo discloses a bearing mechanism built into a femoral component which has a sleeve. The sleeve is disposed at the distal portion of the stem and buttresses a bearing retaining shoulder. Walker in WIPO publication WO 91/03992 discloses a prosthesis with a plastic sleeve having a non-uniform bore.

Despite the recognition and activity directed to solving these longstanding problems, none of the above-identified patents have been widely accepted and prostheses based on these references have not made a significant impact in the field. The problem still exists.

BRIEF SUMMARY OF THE INVENTION

It is an object of the present invention to provide a prosthesis for use in femur replacement surgery which has a modular neck assembly which is selected to provide a predetermined neck length, neck angle and anteversion to meet the unique anatomical requirements of the individual patient and provide the correct force line to transfer the stresses into the anatomical plane of the femur.

It is a further object of the present invention to provide a sleeve on the prosthesis for distal micro motion to avoid stress shielding proximally.

It is yet another object of the present invention to permit the surgeon to provide a prosthesis adapted for the individual patient while maintaining a minimum number of prostheses in stock.

It is still another object of the present invention to provide a prosthesis having a porous coating to facilitate biological in-growth.

In accordance with the teachings of the present invention, there is disclosed a prosthesis for femur replacement surgery having a stem having a vertical axis which is adapted to be received in the femur. The stem has a bore formed therein, the bore being at an angle with respect to the vertical axis of the stem. A modular neck assembly has a first end portion having a length and a second end portion. A socket is formed on the second end portion of the modular neck assembly. Means are provided for receiving a desired length of the first end portion of the modular neck assembly in the bore in an upper portion of the stem and retaining the modular neck assembly therein at a desired neck angle and at a desired degree of rotation therebetween to provide a desired degree of anteversion. In this manner, surgeon may select a desired neck length, neck angle, anteversion and offset for a particular patient undergoing surgery. The prosthesis has an outer surface contacting the femur, the outer surface having thereon a porous coating facilitating biological in-growth with the femur.

In further accordance with the teachings of the present invention, there is disclosed a prosthesis for femur replacement surgery having a stem having a vertical axis which is adapted to be received in a canal formed in the femur. The stem has an upper portion and a lower portion. The lower portion has a uniform diameter and tapers to a point. A unitary sleeve made substantially of metal has a uniform inner diameter slightly greater than the uniform diameter of the lower portion of the stem. The lower portion of the stem is received in the sleeve which is adapted to be press-fitted within the canal in the femur. The lower portion of the stem is circumferentially movable with respect to the sleeve and the stem has micro-motion along the vertical axis of the stem with respect to the sleeve.

In yet another aspect, there is disclosed a prosthesis for femur replacement surgery. A stem has a vertical axis which is adapted to be received in a canal formed in the femur. The stem has an upper portion and a lower portion, the upper portion having an outer surface. A porous coating is formed on the outer surface, the porous coating facilitating biological in-growth with the femur.

In still another aspect, there is disclosed a prosthesis for femur replacement surgery having a stem having a vertical axis which is adapted to be received in a canal formed in the femur. The stem has an upper portion and an opposite lower portion. The upper portion has a blind bore formed therein, the bore being at an angle between 100° and 140° with respect to the vertical axis of the stem. The lower portion is of uniform diameter and tapers to a point. A modular neck assembly has a first end portion and an opposite second end portion, the first end portion being formed at a desired angle with respect to the second end portion. The first end portion of the modular neck assembly is received in the blind bore in the stem such that the second end portion of the modular neck assembly is at a desired angle with respect to the vertical axis of the stem. A first keying means is formed in the blind bore in the stem and a cooperating second keying means is formed on the first end portion of the modular neck assembly such that the modular neck assembly may be rotated to a desired degree of anteversion and inserted into the bore such that the first and second keying means cooperate and rotation of the modular neck assembly within the bore is prevented. A unitary sleeve made substantially of metal has a uniform inner diameter slightly greater than the uniform diameter of the lower portion of the stem. The sleeve is adapted to be press-fitted into the canal in the femur. The lower portion of the stem is received in the unitary sleeve, there being circumferential movement of the lower portion of the stem with respect to the sleeve and the sleeve having micro-motion between the upper portion and the lower portion of the stem.

A method of using the prosthesis is disclosed.

These and other objects of the present invention will become apparent from a reading of the following specification taken in conjunction with the enclosed drawings.

BRIEF DESCRIPTION OF THE DRAWINGS

FIG. 1 is a side elevation view of the assembled prosthesis of the present invention.

FIG. 2 is a back elevation view of FIG. 1.

FIG. 3 is a front elevation view of FIG. 1.

FIG. 11 is an enlarged, partially cut-away, side elevation view showing the embodiment of FIG. 8 received in the bore in the stem.

FIG. 12 is a view of FIG. 1 with the sleeve removed.

FIG. 13 is a cross-sectional view taken across the lines 13—13 of FIG. 1.

DESCRIPTION

Figure 4:
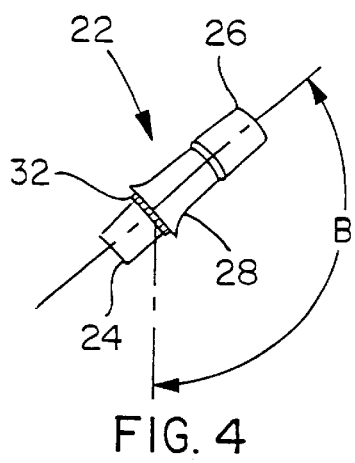
FIG. 4 is a side elevation view of a modular neck assembly showing an angle with respect to the stem.

Referring now to FIGS. 1–3, the prosthesis 10 of the present invention used in femur replacement surgery has stem 12 which has an enlarged upper portion 14 and an opposite lower portion 16. The lower portion 16 preferably is tapered to a point. A sliding sleeve 18 may be received on the lower portion 16 as will be described.

A blind bore 20 is formed in the enlarged upper portion 14 of the stem 12. The center line of the blind bore 20 is formed at an angle with respect to the vertical axis of the stem 12. Means are formed in the bore or around the bore 20 in the surface of the upper portion 14 to rotationally engage and lock a modular neck assembly 22 at a selected degree of rotation within the bore 20 and to prevent any further rotation. The stem 12 may be available in a variety of sizes which have different lengths and which further is designated as small medial aspect, being more narrow in the upper portion 14.

A modular neck assembly 22 (FIGS. 4–5) has a first end portion 24 and an opposite second end portion 26. The length of the second end portion 26 preferably, is greater than the length of the first end portion 24 and may be formed to a desired length. Preferably a flared shoulder 28 is formed between the first end portion 24 and the second end portion 26. The first end portion 24 is formed with a Morse type taper and the bore 20 in stem 12 has a corresponding Morse type taper such that when the modular neck assembly 22 is joined to the stem 12, the modular neck assembly 22 is securely retained therein.

Figure 8:
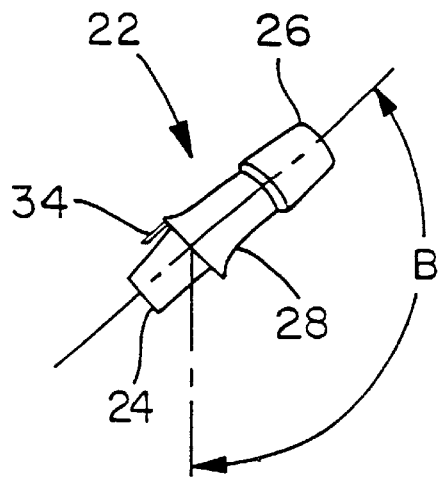
FIG. 8 is a side elevation view of another embodiment of a modular neck assembly showing an angle with respect to the stem.
Figure 9:
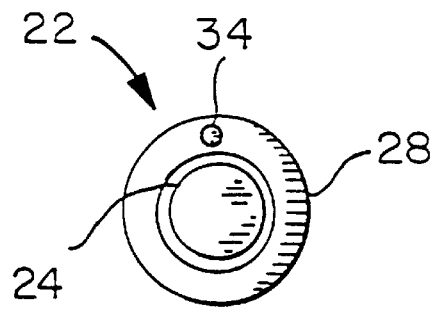
FIG. 9 is an end view of the embodiment of FIG. 8.
Figure 10:
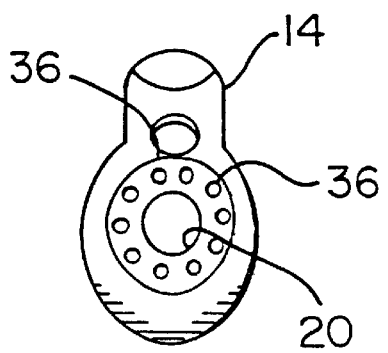
FIG. 10 is an enlarged top elevation view showing the surface and bore of the stem to receive the modular neck assembly of FIG. 8.

In order to provide the surgeon with a modular neck assembly 22 which most nearly corresponds with the anatomy of the patient with respect to the angle between the femur and the hip socket (i.e., customized), the modular neck assembly 22 of the present invention is formed with an angle between the first end portion 24 and the second end portion 26 of the modular neck assembly 22 and, hence the selected angle with respect to the vertical axis of the stem 12. FIGS. 4 and 8 show the angle B ranging from 110° to 140°, although other angles could be provided.

Figure 5:
FIG. 5 is an end view of the modular neck assembly.
Figure 6:
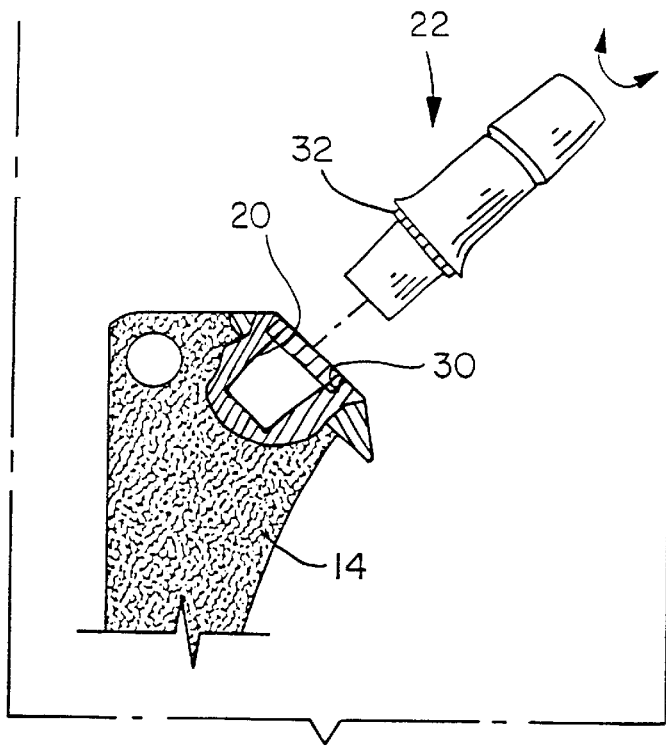
FIG. 6 is an enlarged partially cut away side elevation view of the bore formed in the upper portion of the stem of the prosthesis and the modular neck assembly to be received therein.
Figure 7:
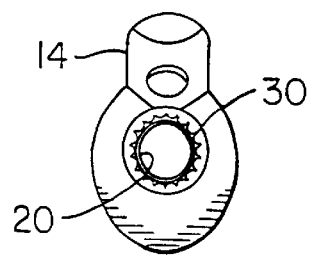
FIG. 7 is an elevation view showing the surface and bore in FIG. 6 to receive the modular neck assembly.

The surgeon is given additional flexibility of configuring the present invention with respect to the anatomical requirements of the patient. The anteversion of the modular neck assembly 22 with respect to the stem 12 is adjustable to a selected angle as required by the individual patient. Anteversion is the angle at which the neck assembly protrudes from the proximal end of the femur. As noted above, means for rotational engagement are formed in or around the bore 20 to engage the modular neck assembly 22 at a selected degree of rotation when the modular neck assembly 22 is disposed in the bore 20. FIGS. 5–7 show one embodiment of the means. A plurality of spaced-apart teeth 30 or similar keying means are formed circumferentially about the bore 20. A complementary plurality of cooperating teeth 32 (or keying means) are formed about the first end portion of the modular neck assembly 22 near the flared shoulder 28. The degree of rotation of the modular neck assembly 22 with respect to the center line of the bore 20 can be selected by the surgeon. This produces the anteversion desired (angle A in FIG. 2). The anteversion can be to the right or to the left of the vertical axis of the stem 12 depending upon the rotation of the modular neck assembly 22 and as shown by the curved arrow in FIG. 6.

Also, when the modular neck assembly 22 is rotated with respect to the bore 20, the modular neck assembly 22 becomes offset with respect to the vertical axis of the stem 12. The offset is the angle formed between the second end portion 26 of the neck assembly and a vertical plane drawn through the bore 20.

Another embodiment of the means for rotational engagement between the bore 20 and the modular neck assembly 22 is shown in FIGS. 8–11. In this embodiment, a peg 34 is formed along a center line of the modular neck assembly 22 and approximately parallel to the first end portion of the modular neck assembly 24. Preferably, the peg 34 depends from the flared shoulder 28. A plurality of spaced-apart peg holes 36 are formed in upper portion 14 of the stem 12. The peg holes 36 are formed radially of the bore 20. Preferably, the peg holes 36 are formed on the surface of the upper portion of the stem but could be within the base of the bore 20 with the peg 34 being formed extending from first end portion 24 of the modular neck assembly. The modular neck assembly 22 is inserted into the bore 20 with the peg 34 being received in a selected peg hole 36 to provide the desired degree of anteversion (right or left).

A further advantage of either embodiment of the means for rotational engagement is that further rotation of the modular neck assembly 22 within the bore 20 is prevented during or after the surgical procedure. In this manner, the surgeon is assured that the prosthesis is customized for the individual patient and is locked in place.

The second end portion 26 of the modular neck assembly 22 has a Morse type taper formed thereon to engage a Morse type taper in a separate socket (not shown) which is placed within the hip of the patient. However, if desired, the second end portion 26 of the modular neck assembly 22 may have formed thereon a spherical head 38. This embodiment may reduce the costs of inventory by avoiding the need to stock additional sockets (FIG. 14).

Figure 16:
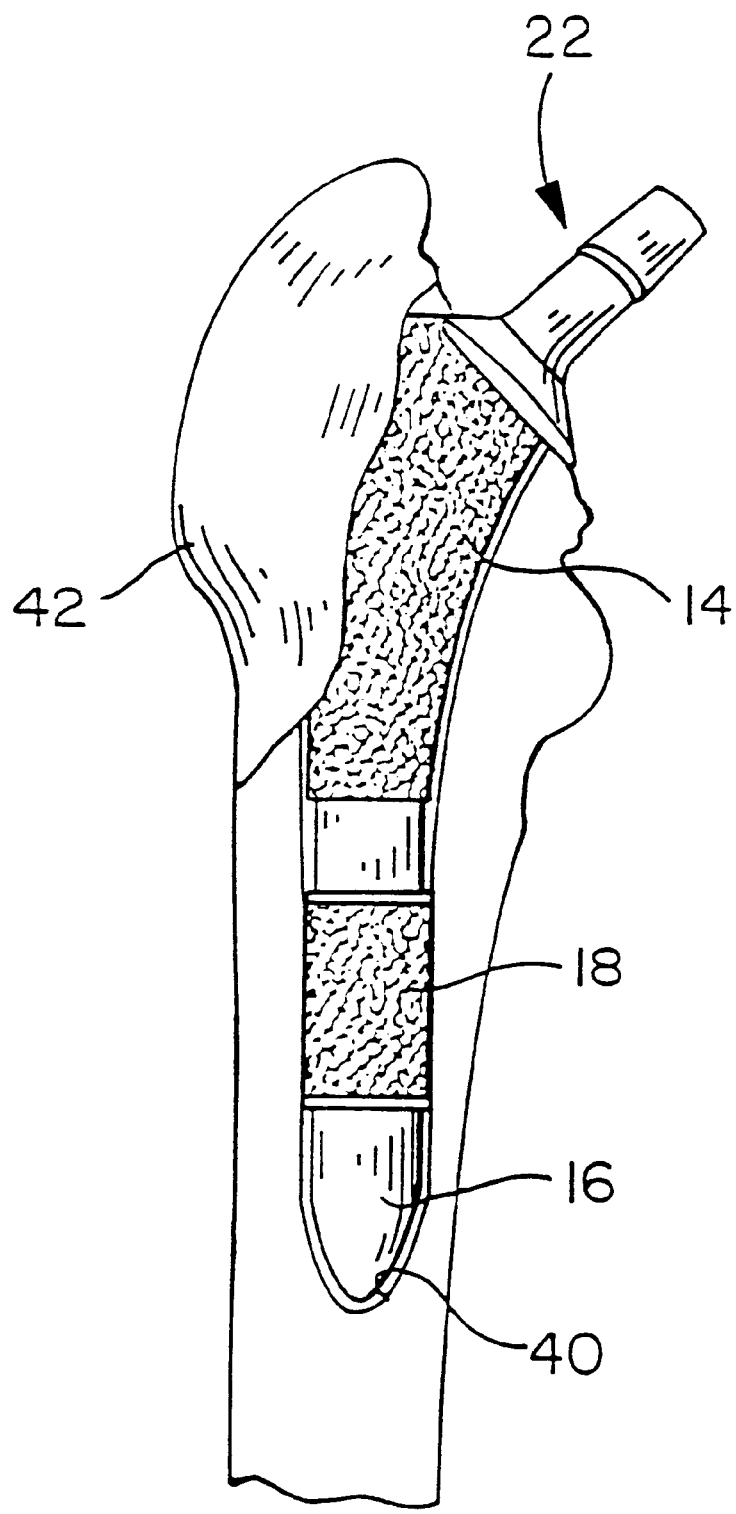
FIG. 16 is a partial cut-away view of the femur having the prosthesis with a sleeve received in the canal in the femur.

The distal end of the stem 12 is tapered to a point which assists the surgeon in directing the prosthesis into the canal formed in the femur. The prosthesis 10 of the present invention may have a lower portion 16 of the stem 12 which has a sleeve 18 received thereon. The sleeve 18 preferably surrounds the circumference near the tip of the lower portion 16 of the stem 12 (FIGS. 1, 2, 12 and 13). The sleeve 18 is unitary which means that the inner circumference of the sleeve is directly opposed to the lower portion of the stem 12 with no intervening members such as a inner sleeve or tube as disclosed in the prior art. Preferably, the sleeve 18 is press-fit into a canal 40 formed in the femur by the surgeon. The canal 40 is formed having a diameter slightly less than the outer diameter of the sleeve 18 at a distance from the top of the canal in the femur which is predetermined by the surgeon. The sleeve 18, when so press-fitted, has a uniform inner diameter which receives the outer diameter of the lower portion 16 of the stem 12 (FIG. 16). An intermediate annular shoulder 44 is formed on the stem 12 at the interface between the upper portion 14 and the lower portion 16. The lower portion 16 of the stem 12 has a uniform diameter above the tapered point. Thus, when the surgeon inserts the stem 12 of the prosthesis 10 into the canal in the femur, the lower portion of the stem 12 is received in the sleeve 18. When the patient moves his/her leg after surgery, the stem 12 may move circumferentially with respect to the implanted sleeve 18 and may also have micro-motion along the vertical axis of the stem 12 with respect to the implanted sleeve 18. Thus, the implanted prosthesis still has motion with respect to the femur so that the stress between the bone and the metal prosthesis is distributed across the entire length of the prosthesis and the proximal femur is not shielded from stress. In this manner, atrophy in the proximal femur is significantly reduced.

It is preferred that a porous coating 46 be applied to the outer surface of the upper portion of the stem 12 and the sleeve 18. The porous coating 46 is formed from metal beads in the range of −40/+65 to −25/+35 mesh size. The beads are formed from the same metal as the prosthesis and are preferred to be cobalt-chrome-molybdenum. The beads are retained onto the outer surface of the prosthesis by a suitable binder and subjected to a sintering process at approximately 2,400° F. in a vacuum furnace. The porous coating is hot isostatic pressed at approximately 15,000 psi at approximately 2,225° F. This porous coating facilitates the biological in-growth and on-growth of cancellous bone to improve the skeletal attachment of an implanted device such as the prosthesis used in orthopedic surgery. The addition of hydroxyapatite to the surface of the spherical beads enhances biological in-growth. The biological in-growth effects an anchoring of the prosthesis to the femur.

Figures 14, 15:
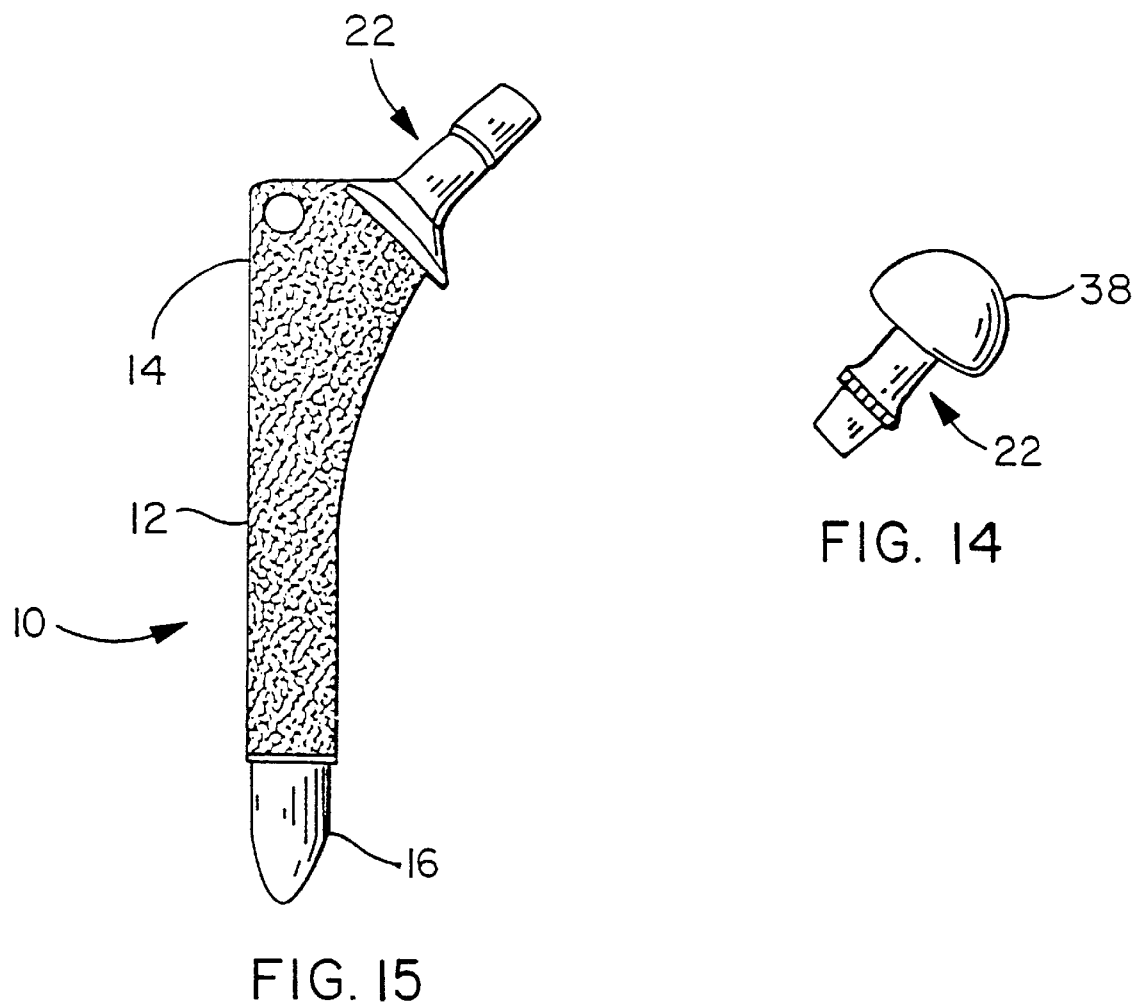
FIG. 14 is a side elevation view of the modular neck assembly having a spherical head formed on the second end portion.
FIG. 15 is a side elevation view of the prosthesis of the present invention which does not have a sleeve.

FIG. 15 shows a prosthesis 10 without a sleeve and having a porous coated surface extending onto the lower portion of the stem.

In use, the surgeon carefully measures the angle between the patient's femur and hip socket and the degree of anteversion of the patient's femur. Also, the length of the patient's legs are carefully measured. Based on these measurements the surgeon meticulously calculates the type of prosthesis required for the particular patient. The surgeon forms a canal in the patient's femur, the canal having a predetermined diameter. If desired a sleeve 18 is press fitted into the canal in the femur at a predetermined distance from the top of the canal. A modular neck assembly 22 is selected having an angle between the second end portion 26 and the vertical axis of the stem 12 which most closely corresponds with the angle between the patient's hip socket and the femur. The modular neck assembly 22 is rotated with respect to the bore 20 in the stem 12 which most closely corresponds with the degree of anteversion of the patient's femur. The modular neck assembly 22 is inserted into the bore 20 to secure the modular neck assembly 22 to the stem 12 as the predetermined angle and degree of anteversion. The stem 12 with the modular neck assembly 22 inserted into the canal in the femur and is received in the sleeve 18 (if present). The prosthesis 10 is connected to the hip socket.

Preferably, the entire prosthesis, including the stem 12, the modular neck assembly 22 and the sleeve 18 are formed substantially from metal. A preferred metal is a cobalt-chrome-molybdenum alloy which is very compatible with the tissue and bones of human beings. The prosthesis is not limited to this metal but may be made of other metals including titanium.

Thus, this present invention provides a prosthesis which more closely reproduces the anatomy of the individual patient. It enables the surgeon to maintain a smaller inventory of components while providing a greater versatility in sizes. This results in a cost reduction. The components of the prosthesis are amenable to mass production which further reduces unit costs. Furthermore, the prosthesis with the sleeve avoids stress and atrophy in the femur after implantation.

Obviously, many modifications may be made without departing from the basic spirit of the present invention. Accordingly, it will be appreciated by those skilled in the art that within the scope of the appended claims, the invention may be practiced other than has been specifically described herein.

What is claimed is:

1. In an implanted prosthesis for femur replacement surgery, the prosthesis having an overall length, the prosthesis including a sleeve configured to be substantially fixed within a canal in a proximal portion of the femur, and the prosthesis further including a stem having a lower portion slidably received in the sleeve, the lower portion of the stem having a given axial length defined between an annular shoulder on the stem and a distal tip portion thereof, the improvement comprising the combination of:

the sleeve being unitary and made substantially of metal having an outer surface and a uniform inner diameter, the axial length of the sleeve being substantially less than the given axial length of the lower portion of the stem, such that the stem may have substantial axial movement within the sleeve consonant with rotational movement therein, and such that the sleeve will likely not abut against the shoulder on the stem, whereby the stress between the femur and the prosthesis is distributed over substantially the entire overall length of the prosthesis, whereby the proximal portion of the femur is not shielded from stress, and whereby patient atrophy adjacent to the proximal portion of the femur is significantly reduced, the stem having an upper portion opposite from the lower portion, the upper portion having a blind bore formed therein, the bore being at an angle between 100° and 140° with respect to the vertical axis of the stem, a selected modular neck assembly having a first end portion and an opposite second end portion, the first end portion of the modular neck assembly being formed at a desired angle with respect to the second end portion, the desired angle being adapted to a specific patient, the first end portion of the modular neck assembly being received in the blind bore in the stem such that the second end portion of the modular neck assembly is at a desired angle with respect to the vertical axis of the stem, a first plurality of rotational prevention means formed circumferentially about the blind bore in the stem and a cooperating second plurality of rotational prevention means formed circumferentially about the first end portion of the modular neck assembly such that the selected modular neck assembly may be rotatably positioned to a desired degree of anteversion and inserted into the bore such that the first and second rotational prevention means cooperate and rotation of the modular neck assembly within the bore is prevented, and the prosthesis is adapted for the specific patient.

* * * * *